United States Patent [19]
Ash

[11] Patent Number: 5,277,820
[45] Date of Patent: Jan. 11, 1994

[54] DEVICE AND METHOD FOR EXTRACORPOREAL BLOOD TREATMENT

[75] Inventor: Stephen R. Ash, Lafayette, Ind.

[73] Assignee: Hemocleanse, Inc., West Lafayette, Ind.

[21] Appl. No.: 832,080

[22] Filed: Feb. 6, 1992

[51] Int. Cl.$^5$ .................................. B01D 61/00
[52] U.S. Cl. .................. 210/646; 210/117;
210/195.2; 210/196; 210/257.1; 210/258;
210/321.6; 210/321.67; 210/321.75;
210/321.84; 210/650; 210/651; 210/660;
210/694; 422/101; 436/178; 604/4; 604/5;
604/6
[58] Field of Search ............... 210/645, 646, 647, 650,
210/651, 655, 660, 694, 929, 723, 728, 729, 749,
767, 805, 744, 104, 117, 136, 195.2, 196, 205,
219, 257.1, 258, 321.6, 321.67, 321.68, 321.71,
321, 75, 321.84, 502.1; 604/4, 5, 6; 436/178;
422/101

[56] References Cited

U.S. PATENT DOCUMENTS

| | | | |
|---|---|---|---|
| 4,024,059 | 5/1977 | Sausse | 210/195.2 |
| 4,071,444 | 1/1978 | Ash et al. | 210/321.84 |
| 4,343,705 | 8/1982 | Legg | 210/321.84 |
| 4,348,283 | 9/1982 | Ash | 210/321.67 |
| 4,581,141 | 4/1986 | Ash | 210/321.84 |
| 4,597,868 | 7/1986 | Watanabe | 210/321.84 |
| 4,767,526 | 8/1988 | Vantard | 210/321.71 |
| 4,897,189 | 1/1990 | Greenwood et al. | 210/195.2 |

Primary Examiner—Robert A. Dawson
Assistant Examiner—Sun Uk Kim
Attorney, Agent, or Firm—Woodard, Emhardt, Naughton, Moriarty & McNett

[57] ABSTRACT

Disclosed are preferred devices and methods which provide extracorporeal treatment of blood to effectively and consistently remove toxins therefrom and from patients over extended periods of time.

21 Claims, 6 Drawing Sheets

DEVICE AND METHOD FOR EXTRACORPOREAL BLOOD TREATMENT

BACKGROUND OF THE INVENTION

This invention generally relates to devices and methods for extracorporeally treating blood to selectively remove toxins therefrom.

By way of background, extensive efforts have been made to discover safe and effective methods for removing toxins from patients by extracorporeal treatment of their blood. These efforts have included many studies directed to methods for extracorporeal treatment of hepatic failure due to infection, cirrhosis, toxin damage or other causes. Many methods have been proposed with the goal of removing small molecular toxins, protein-bound molecules or larger molecules thought to be responsible for the coma and illness of hepatic failure. Thus far, evidence has been presented supporting adverse effects caused by non-protein bound small molecules such as ammonia, phenols, mercaptans, short chain fatty acids, aromatic amino-acids, neural inhibitors (GABA, glutamate), false neural transmitters (octopamine) and bile salts. Protein-bound bilirubin and bacterial endotoxins are large molecules which are toxic, but generally not thought to be responsible for the coma and illness of hepatic failure. Nevertheless, many hepatologists have tended to ignore the small molecules and remove the large toxins by various means.

As to specific modes of treatment, those previously proposed and used have included blood perfusion over heterogeneous liver pieces or past membranes which contact hepatocytes. Also proposed and used have been hemoperfusion through columns of coated activated carbon or macroreticular resins, blood exchange, plasmapheresis with plasma replacement, plasmapheresis with plasma perfusion through bilirubin-binding and aromatic amino acid-binding sorbents, standard hemodialysis, standard hemodialysis with an amino acid dialysate and plasma exchange, high permeability hemodialysis, dialysis with charcoal-impregnated membranes, continuous hemofiltration, peritoneal dialysis, oral sorbents and many other therapies.

While some of these previously proposed treatments have produced neurological improvement in stage 2 or 3 coma and have aided hepatic regeneration after injury, they have not provided much clinical improvement in patients in stage 4 coma on respirators. Additionally, these diverse treatments each produce adverse effects on the patient, offsetting benefits. See, generally, Ash, S. R., Treatment of Acute Hepatic Failure With Encephalopathy: A Review, *Int. J. of Artif. Organs*, Vol. 14, pp. 191-195 (1991).

For example, although daily charcoal hemoperfusion has been shown to provide neurologic and physiologic improvement of patients with hepatic failure and coma, Winchester, J. F., Hemoperfusion, in Replacement of Renal Function by Dialysis (Maher, J. F., ed.), Dordrecht:Kluwer Academic Publishers, pp. 439-459, (1989), hemoperfusion nevertheless requires systemic anticoagulation and also depletes coagulation factors and platelets from the blood. Moreover, the relatively large sorbent granules used in hemoperfusion columns have limited surface area (about 1000-10,000 m$^2$). Consequently, the available sorbent surface area is saturated within a few hours, clearance of bound chemicals rapidly diminishes, and a new column must be used. Furthermore, clinical benefits of charcoal hemoperfusion may be offset by deleterious effects of bio-incompatibility. In one instance, a controlled study of patients with fulminant hepatic failure, all treated with aggressive intensive care including intracerebral pressure monitoring, demonstrated that patients treated by hemoperfusion had a generally lower survival rates than those treated with aggressive intensive care alone. The only exception was noted in patients having fulminant hepatic failure due to hepatitis A or B, for whom there was reported a "trend toward improved survival" when treated with charcoal perfusion. O'Grady, J. G. et al., Controlled Trials of Charcoal Hemoperfusion and Prognostic Factors in Fulminant Hepatic Failure, *Gastroenterology*, Vol. 94, pp. 1186-92 (1988).

As mentioned, standard hemodialysis (i.e. dialysis of blood against only a dialysate solution) has also been studied as a possible treatment for hepatic failure. However, benefits of hemodialysis may be similarly obscured by removal of substances (e.g. urea) known not to be toxins of hepatic failure. Additionally, hemodialysis requires the use of large volumes of dialysate solution which limits the mobility and increases the complexity of the machines, or alternatively, it requires the provision of a sorbent column to "regenerate" the dialysate.

It is in light of this extensive background that the applicant entered his study, and has now discovered a simple and efficient method and device for extracorporeal blood treatment which can be used safely, effectively and conveniently in various thereapeutic regimens.

SUMMARY OF THE INVENTION

One preferred embodiment of the invention provides a method for extracorporeal treatment of blood to effectively and consistently remove toxins therefrom over an extended period of time. The method includes the steps of passing the blood through a blood side of a plate dialyzer having a blood inlet to and a blood outlet from a blood side separated from a dialysate side by dialyzer membranes, the plate dialyzer further having a dialysate inlet to and dialysate outlet from said dialysate side. Further, the dialyzer membranes are compliantly formed to expand and compress in response to alternating negative pressure and positive pressure on the dialysate side of the dialyzer. The method also includes passing a sorbent suspension through the dialysate side so as to selectively dialyze the toxins of the blood across the membranes. Movement of both blood and suspension are caused by the application of alternating negative and positive pressure on the dialysate side so as to expand and contract the dialyzer membranes and agitate the sorbent suspension to prevent settling and mix it to maintain chemical gradients across the membrane. A positive pressure gradient is maintained throughout the cycle from the blood side to the dialysate side of the dialyzer. Preferred modes of practicing this embodiment of the invention involve a method for extracorporeal treatment of hepatic failure or drug overdose, and for "pulse" treating a patient with a thereapeutic agent, for example an anti-cancer or anti-viral agent. This pulse treatment method includes the steps of administering a dose of the agent to the patient, and removing the administered agent by the novel extracorporeal blood treatment described above. In this manner, toxicity of a treatment of a given efficacy can be reduced.

Another preferred embodiment of the invention provides a dialysis instrument. The dialysis instrument includes a plate dialyzer having a blood inlet to and a blood outlet from a blood side separated from a dialysate side by dialyzer membranes. The plate dialyzer further has a dialysate inlet to and dialysate outlet from the dialysate side, and the dialyzer membranes are compliantly formed to expand and compress in response to alternating negative pressure and positive pressure on the dialysate side of the dialyzer. The instrument also has dialysate circulating means for circulating dialysate through the dialysate side of the dialyzer in a direction generally from the dialysate inlet to the dialysate outlet. The dialysate circulating means includes an accumulator reservoir operable to alternately accumulate and expel dialysate to apply alternating negative pressure and positive pressure on the dialysate side of the dialyzer. Thereby, the expansion and contraction of dialyzer membranes is caused while a positive pressure gradient from the blood side to the dialysate side of the dialyzer is maintained. The instrument also has blood circulating means for circulating blood through the blood side of the dialyzer in a direction generally from the blood inlet to the blood outlet. The blood circulation is powered by the expansion and contraction of dialyzer membranes caused by alternating negative and positive pressure on the dialysate side of the dialyzer, and thus no blood-side pump is needed.

Additional objects and advantages of the present invention will be apparent from the description which follows.

DESCRIPTION OF THE PREFERRED EMBODIMENT

Figure 1:
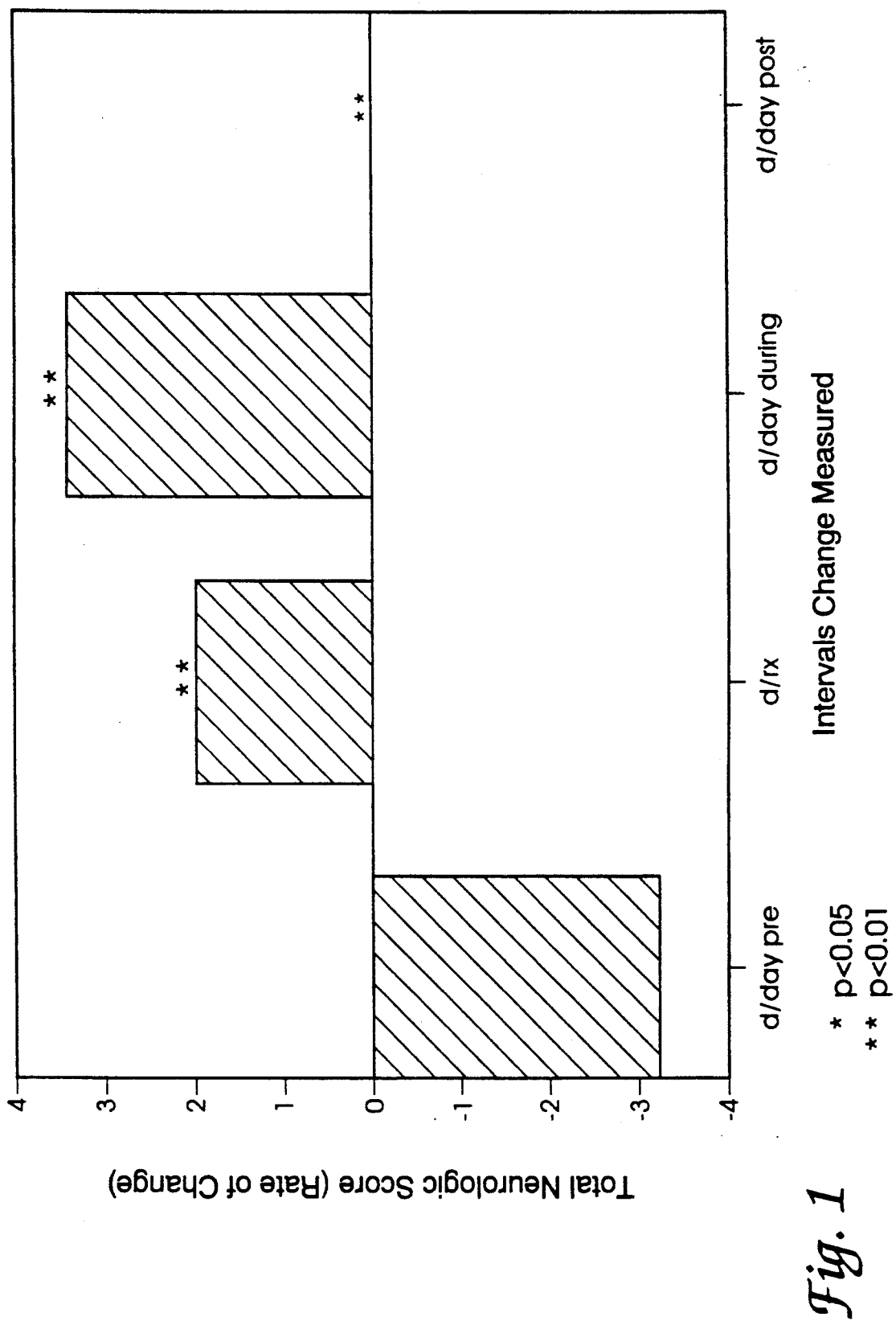
FIG. 1 presents the average change in neurologic status of hepatic failure patients during individual treatments (d/rx) and in the days before, during, and after treatment (d/day pre, during, post) by the method of the invention.

For the purposes of promoting an understanding of the principles of the invention, reference will now be made to certain embodiments and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention relates.

As indicated above, one preferred embodiment of this invention relates to a method for extracorporeal treatment of blood in a manner which provides the safe, consistent and effective removal of toxins over extended periods of time.

The sorbent suspension used in the invention will usually include powdered surface adsorptive agents, physiologic electrolytes and macromolecular flow inducing agents. In general, these components are present in effective amounts to achieve the desired removal of substances from and electrolyte balance in the blood of the patient while maintaining the stability and fluidity of the sorbent suspension.

The powdered surface adsorptive agent can be any one of many known to those practiced in this area, but is preferably powdered activated charcoal. Further, the powdered surface adsorptive agent preferably has an average particle diameter of not greater than about 100 microns. More preferably, this average particle diameter is less than about 50 microns, with 90% or more of the particles having diameters not greater than about 75 microns. Particles exceeding 75 microns in diameter can be screened if necessary. As one example, a suitable finely powdered activated charcoal is available from American Norit Company, Inc. of Jacksonville, Fla. U.S.A., which can be screened to remove particles larger than those desired.

The macromolecular flow inducing agent functions to maintain the stability of the sorbent suspension formulation (i.e. helps to prevent solids from settling out of suspension) and maintains the flow properties of the suspension. One desirable flow inducing agent is a nonionic, hydroxyl-containing polymer such as a glycol derivative. Suitable agents of this type are available from BASF Wyandotte of Parsippany, N.J., U.S.A. under the trademark "Pluronic" polyols. These Pluronic polyols are polyoxyalkylene derivatives of propylene glycol. To date, applicant has used Pluronic F68, which functions both as a flow inducing agent and a defoaming agent. Another flow agent that has been included in preferred suspensions is macroreticular polyvinylpyrrolidone.

The types and amounts of electrolytes included in the suspension formulation will depend upon the specific needs of the patient and will be readily determinable by physicians or others skilled in the area. Typically, the electrolytes will include sodium and chloride (e.g. optionally provided as sodium chloride), and can also include bicarbonate, potassium, calcium, or any other electrolytes to be regulated in the patient. As indicated, however, the types and amounts of electrolytes may vary widely depending on patient needs.

The sorbent suspension formulation may also include an ion-exchanger to bind ionic chemicals, e.g. ammonium, etc., which may occur in the patient's blood. Many suitable ion exchangers including both resins and other materials such as zeolites are known in the art. When included, the ion-exchanger is preferably a cation-exchange resin, which is desirably loaded with sodium or calcium. For example, to date, sodium polystyrene sulfonate has been a preferred material.

The surface adsorptive agent, electrolytes, flow inducing agents and any other additives will usually comprise about 5% to 30% by weight of the sorbent suspension formulation as a whole, with the remainder being water. Typically, solid sorbents will comprise about 2% to 25% by weight of the suspension formulation, and electrolytes will comprise about about 1% to 5% of the suspension formulation. Within these parameters, more preferred sorbent suspension formulations comprise about 2% to 20% powdered surface adsorptive agent, up to about 10% ion-exchanger, and up to about 1% flow agent such as a polyol and/or polyvinylpyrrolidone.

There are many dialyzer membranes which are known for use in dialyzing body fluids such as blood, and those skilled in the area will be readily able to select and utilize a suitable membranes in the present invention. One suitable membrane is a cellulosic membrane, particularly one composed of regenerated cuproammonium cellulose (Cuprophan).

The inventive methods are advantageously performed in a preferred, dialysis instrument including a parallel plate dialyzer and moving the sorbent suspension formulation in a counter-current mode by the direct application of alternating negative pressure and positive pressure on the dialysate side, as described in more detail in Example 1 below. The preferred dialysis system also creates a slight back and forth motion of the sorbent suspension formulation in the dialyzer, which agitates, locally mixes, and helps to prevent settling of the suspension.

As indicated above, the inventive extracorporeal blood treatment can be used to safely and effectively treat the coma and illness of hepatic failure, and almost always improves the patient's clinical condition as evidenced by improved physiologic and neurologic patient status. For instance, Example 2 below describes a study in which fifteen patients with acute hepatic failure were treated by the above-described method for blood treatment. The patients were in very serious and declining clinical condition due to acute hepatic failure with ensuing stage 3 or 4 coma. In some patients, hepatic failure was precipitated by a complication such as bleeding or sepsis occurring during the course of chronic hepatic insufficiency. Each of the patients had adverse conditions other than hepatic failure, including heart failure, kidney failure, respiratory failure, sepsis, etc., making them even more complex than patients included in previously reported studies of fulminant hepatic failure and its expected complications. Nevertheless, upon treatment, neurologic improvement occurred in thirteen of the fifteen patients (see also FIG. 1 which gives average rate of change of neurologic scores), and physiologic improvement also in thirteen of the patients.

Figure 2:
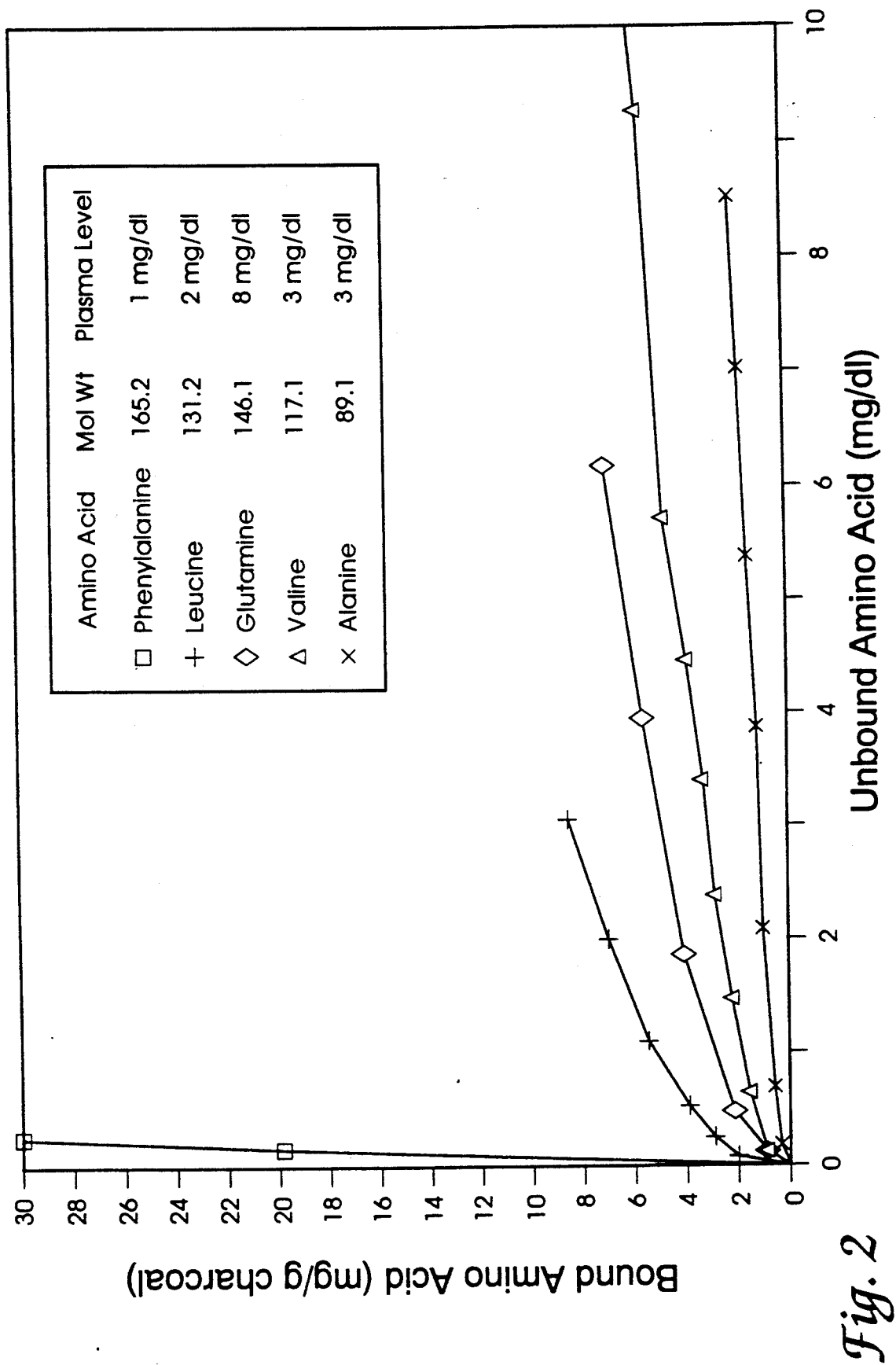
FIG. 2 is a graph of charcoal bound amino acid (milligrams/gram charcoal) versus unbound amino acid concentration (milligrams/deciliter) for phenylalanine, leucine, glutamine, valine and alanine.

Patients in hepatic failure often develop an excessive blood concentration of aromatic amino acids as compared to branch chain amino acids. As is illustrated in FIG. 2, one advantage of the inventive method is its ability to remove aromatic amino acids from the patient more rapidly and effectively than it removes branch chain amino acids. FIG. 2 charts bound amino acid (milligrams/gram charcoal) versus unbound amino acid-concentration (milligrams/deciliter) for phenylalanine, leucine, glutamine, valine and alanine. As shown, the powdered charcoal adsorbs the aromatic amino acid, phenylalanine, in a highly selective fashion as compared to the aliphatic amino acids. Thus, when used, the inventive blood treatment method can help maintain a balance of the aromatic and branch chain amino acids in the patient. Furthermore, the sorbent suspension formulations can be loaded with branch chain amino acids or other biological components prior to or during use, whereby branch chain amino acids or other biological components are more selectively left in, or even provided to the patient.

It has also been discovered that the method of this invention can be successfully used in treating drug overdose, even with highly-protein-bound drugs (i.e. drugs which are 75% or more protein bound). For instance, as Example 4 below illustrates, a patient subjected to a large overdose of a tricyclic antidepressant, upon treatment in accordance with the invention, rapidly recovered. This is despite the fact that the drug was over 90% protein bound, and all other conservative treatments had left the patient in a declining condition. Thus, the invention method has demonstrated highly surprising efficacy in the treatment of patient overdose even with highly protein bound drugs.

In another mode, the blood treatment method of the invention can be used in a novel method for "pulse" therapy with a thereapeutic agent. As background, many therapeutic agents have a low therapeutic margin. Dosages necessary to create benefits are only slightly below those causing unacceptable toxicity. For instance, the toxicity of most chemotherapeutic agents is related to the product of blood level times time (area-under-the-curve of a graph of blood concentration vs. time).

Using the invention method in conjunction with cancer chemotherapy or other pulse therapy can radically alter the pharmacokinetics of the agents employed. The ability of the inventive method to add clearance to the body's clearance can greatly increase the rate elimination of the agent. Further, the removal of the agent by the inventive method is not associated with production of by-products and metabolites, as does removal by the liver and/or kidney. As a result, the toxicity of a given dose may be significantly reduced. This means that administration of higher dosage amounts to create a higher peak blood level can be coupled with the inventive dialysis step to maintain the same area-under-the-curve (i.e. toxicity) as in patients given a smaller dose without use of the invention. Thus, a greater therapeutic effect may be achieved with approximately the same toxicity, or the same therapeutic effect may be achieved with reduced toxicity.

Thus far, the inventive method has proven highly effective in removal of chemotherapy agents such as Cisplatin and Methotrexate from blood, although many other agents which are extractable by the blood treatment method will also be suitable for the invention.

The invention will now be described with reference to the following specific Examples which are illustrative, and not limiting, of the invention.

EXAMPLE 1

Figure 3:
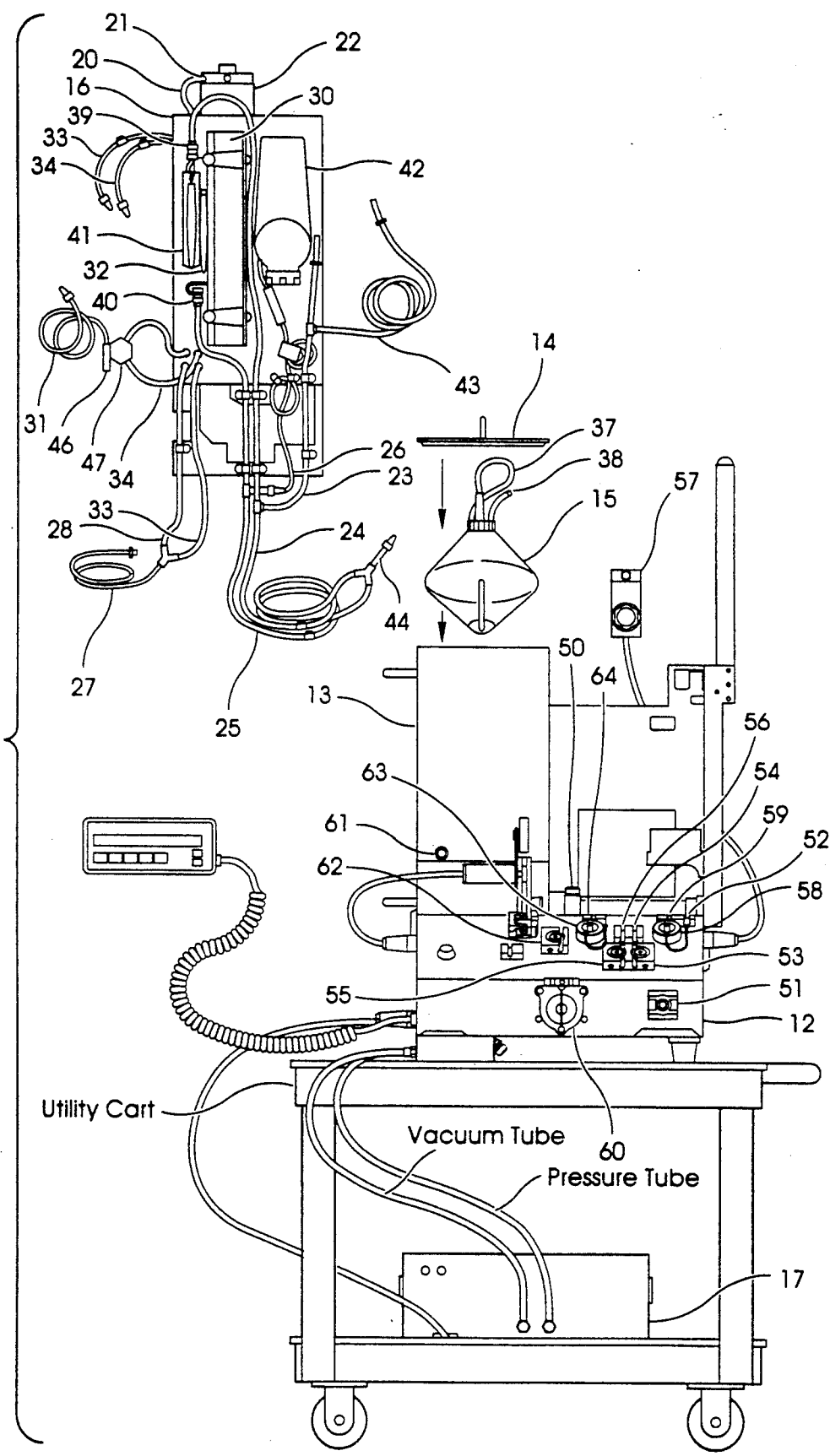
FIG. 3 is a perspective view of a preferred pressure/vacuum operated dialysis system of the invention.

Operation and Components of Preferred Vacuum/Pressure Operated Flow-Through Dialysis System FIG. 3 is a perspective view of a preferred dialysis system 11 sitting on a standard hospital cart. Generally, the preferred dialysis system 11 is similar in some respects to the dialyzer disclosed in my earlier U.S. Pat. No. 4,661,246 issued Apr. 28, 1987, which is hereby incorporated herein by reference. However, to fill and empty the dialyzer of blood, the present system uses the direct application of pressure and vacuum to give positive and negative pressure changes in the dialysate. This increases the blood flow and enhances the mixing of the sorbent suspension formulation, as well as helps to maintain optimal chemical gradients across the dialysis membrane.

Figure 4:
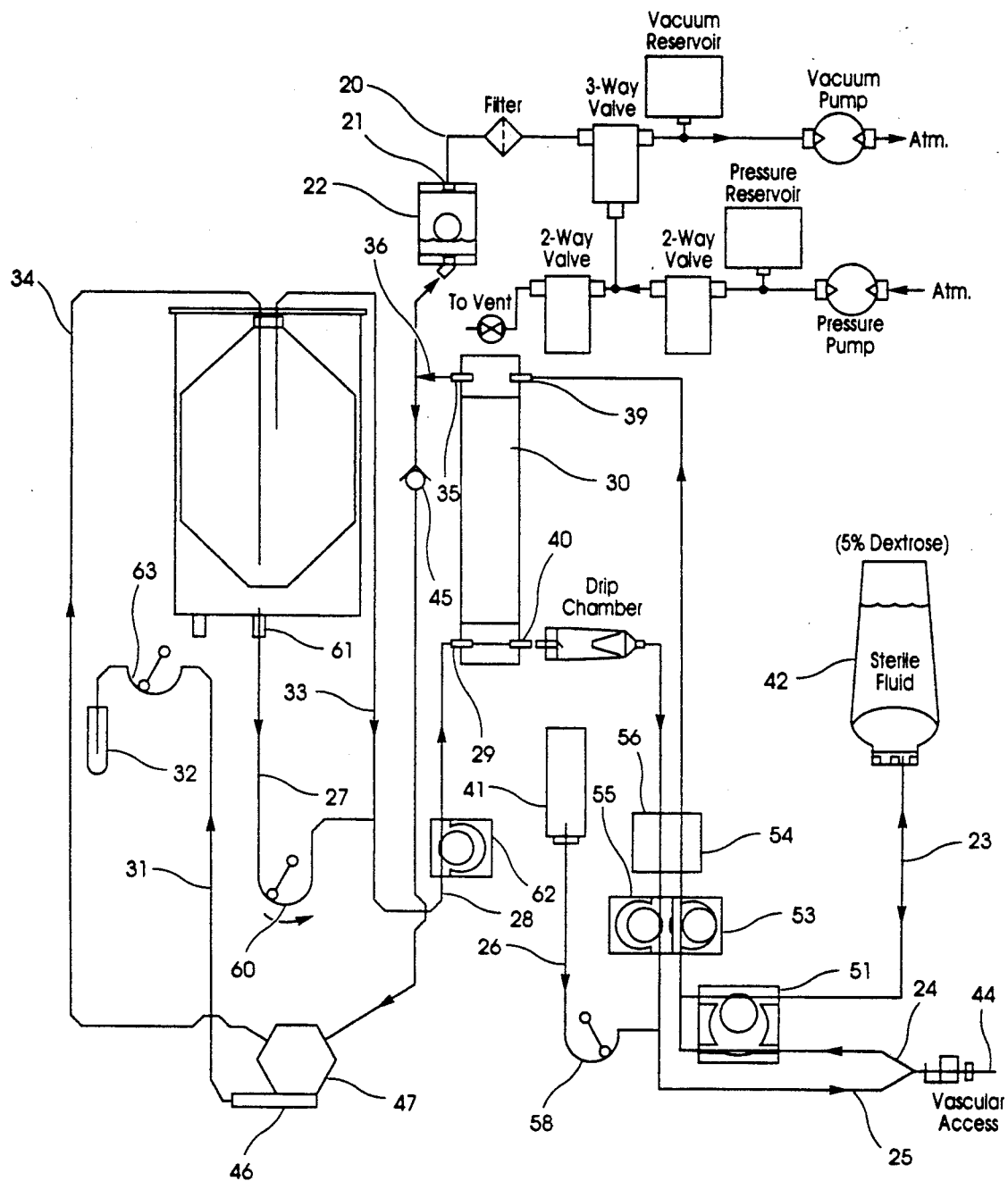
FIG. 4 is a schematic representation of the hydraulic system of the dialysis system of FIG. 3.
Figures 5A, 5B:
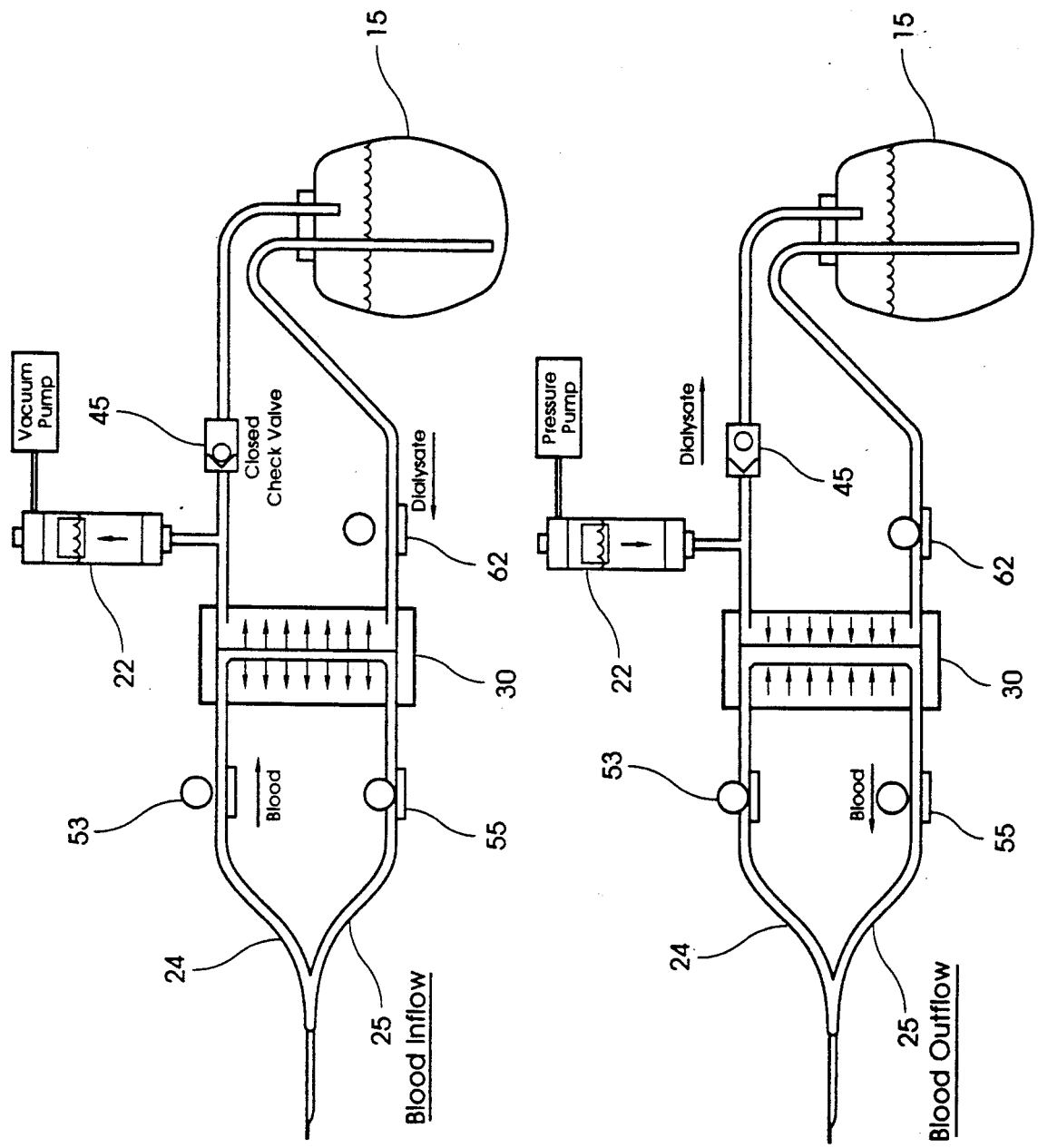
FIG. 5(A, B) is a schematic representation of the mechanics of operation of the preferred direct pressure/vacuum operated dialysis system of FIG. 3.

With continued reference to FIG. 3, the dialysis system 11 includes a machine base 12, reservoir tank 13 with cover 14, a sorbent bag 15 containing sorbent suspension materials, disposable pack 16 (including the plate dialyzer), and power supply 17 (providing vacuum, pressure, and DC power to the machine base). Referring now also to FIGS. 4 and 5, FIG. 4 is a hydraulic schematic of the dialysis system, and FIG. 5 provides in parts A and B a summary of the mechanics and hydraulics of operation of the system during blood inflow and outflow, respectively. Generally, in the following discussion, the numbers 20–47 will be used to designate components on the disposable pack 16, whereas numbers 50 and above will designate components of the machine base 12. In FIG. 3, the machine base 12 and disposable pack 16 are shown separated. Of course, in use together, the pack 16 is mounted to machine base 12 and their respective components assembled generally as follows.

Vacuum/pressure line 20 from top port 21 of accumulator 22 is connected to vacuum pressure port 50 on machine base 12 which feeds vacuum and pressure from the respective sources thereof in power supply 17. Prime tube 23 is seated into the upper side of prime/rinse clamp 51 and through prime fluid sensor 52. The blood inflow tube 24 is seated into the lower side prime rinse clamp 51, blood inflow clamp 53 and the blood inflow sensor 54. The blood outflow tube 25 is seated into blood outflow clamp 55 and blood outflow sensor 56, and fluid level sensor 57 is placed onto accumulator 22. Reinfusate tube 26 is loaded into reinfusate pump 58 and reinfusate fluid sensor 59. Dialysate tube 27 (prior to the "Y" split) is loaded into dialysate pump 60 and its end connected to water port 61. Branch of dialysate tube 28 (after the "Y" split) which connects to the dialysate inlet 29 of dialyzer 30 is seated into dialysate-in clamp 62. Filtrate line 31 is loaded into filtrate pump 63 and into filtrate fluid sensor 64. Filtrate line 31 is also connected to filtrate disposal bag 32 which is vented. Three liters of sterile water are added to reservoir tank 13. Sorbent bag 15 is suspended from reservoir cover 14. Tubes 33 (leading to dialysate inlet 29) and 34 (leading to the exit port of accumulator 22 and also connected to dialysate outlet 35 via line 36) are connected to lines 37 and 38 provided on and leading into sorbent bag 15.

The following steps are conducted under sterile conditions. Blood inflow line 24 and blood outflow line 25 are connected to blood inlet 39 and blood outlet 40 of dialyzer 30, respectively. Reinfusate solution (e.g. $CaCl_2$ solution and appropriate amounts of KCl and/or NaCl solution) is injected into reinfusate bag 41. Reinfusate line 26 is connected to reinfusate bag 41 and a drip chamber in the line is partially filled. Prime tube 23 is connected to prime bottle 42 containing priming fluid, e.g. 5% dextrose. If desired, replacement fluid can be provided via fluid replacement line 43.

Thus, after the above assembly, the blood inflow 24 and blood outflow 25 tubes pass from a single access line 44 through clamps 53 and 55 and optical monitors 54 and 56 to connect to the top 39 and bottom 40 openings of the blood side of the dialyzer 30. Cylindrical accumulator 22 attaches to the dialysate space at the top opening 35 of the dialysate side of dialyzer 30, and alternating strong vacuum (i.e. negative pressure) and modest positive pressure in accumulator 22 (provided by line 20 through port 21 above the fluid level) alternately draws dialysate into and expels dialysate from accumulator 22, which expands and compresses the membranes of dialyzer 30 (as illustrate by the arrows, FIG. 5), while the automatically controlled blood inflow and outflow clamps 53 and 55 assure that blood passes unidirectionally through the dialyzer 30, at an average rate of up to 250 ml/min (in 5 cycles). The ratio of inflow/outflow cycle times determines the ultrafiltration rate, from a minimum of about 200 ml/hr at a ratio of about 1.45, to about 600 ml/hr at a ratio of 2.45.

In the preferred dialysis system 11 utilized in the specific Examples, the dialyzer was a 1.6m$^2$ COBE parallel screen-plate dialyzer having dialysis membranes composed of regenerated cuproammonium cellulose (Cuprophan) and having a functional molecular weight cut-off of about 3000 daltons, i.e. only molecules of about 3000 daltons or less will pass through the membrane.

As opposed to many previously-known dialysis systems, the system used in the invention contains a sorbent suspension in the dialysate instead of merely a dialysis solution. Flow of the suspension is generally countercurrent, and is both bidirectional between the accumulator 22 and dialyzer 30, and circular between the dialyzer 30 and sorbent reservoir 15.

Figure 6:
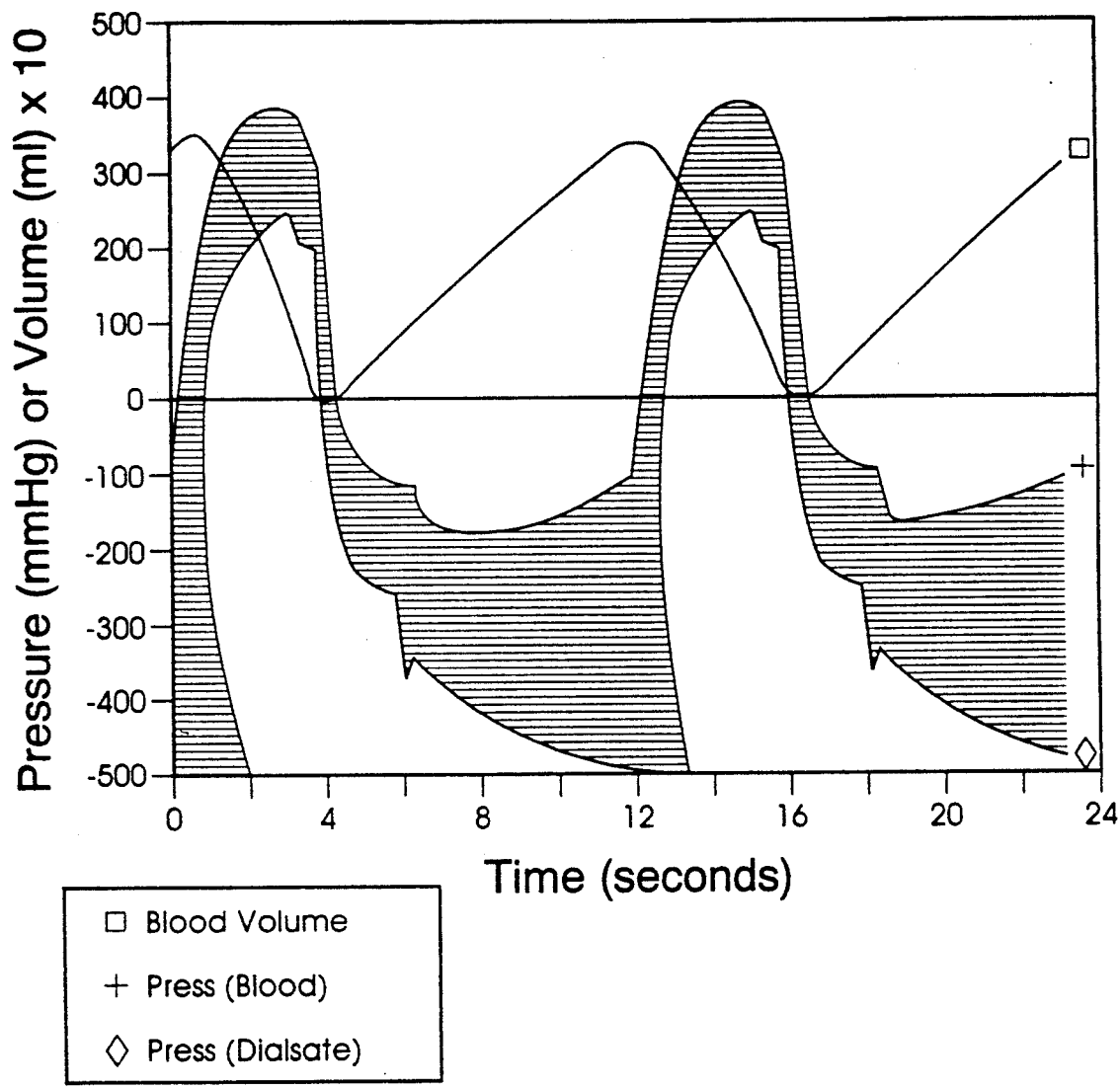
FIG. 6 is a graph showing dialysate side pressure, blood side pressure, and blood volume in the dialyzer of the dialysis system of FIG. 3 during typical cycles.

In summary, during the first part of blood inflow (see particularly FIG. 5A), clamp 62 on the dialysate inflow line 33 opens, allowing sorbent suspension to flow from the sorbent reservoir 15 through the entire dialyzer 30, filling the accumulator 22 to the level of sensor 57. Clamp 62 then closes and remains closed during the remainder of inflow and all of outflow (see particularly FIG. 5B), when pressure in the accumulator 22 returns some suspension to the dialyzer 30 and passes some through one-way valve 45 to return to the reservoir 15 via dialysate return line 34. In typical operation, each minute, about 900 ml of sorbent suspension flows into accumulator 30 (in 5 cycles). 600 ml of sorbent suspension flows back into the dialyzer 30, and 300 ml flows from the accumulator 22 into the sorbent reservoir 15. This, along with the expansion and contraction of the dialyzer membranes, keeps the sorbent suspension well mixed at the dialyzer membrane surface. Typical blood side and dialysate side pressure, and the blood volume of the dialyzer over time during such operation are shown in FIG. 6. As can be seen, both the blood side and dialysate side pressures alternate between positive and negative pressure, while the spring action of the plate dialyzer membranes ensures that there is constantly a positive pressure gradient from blood side to dialysate side.

In the preferred system, sorbent bag 15 initially contains dry sorbent materials to which the system automatically adds 1.5 liters of sterile water from reservoir tank 13 via port 61 during priming. This operation is powered by dialysate pump 60. For the Examples given below, the sorbent materials in bag 15 were as follows:

140 grams powdered activated charcoal (300,000 square meters surface area, between 5 and 53 micron mean particle diameter, 70 micron maximum particle diameter)

80 grams cation exchanger (sodium polystyrene sulfonate, PSS, functional binding of 80 mEq).

1.5 grams Pluronic F68.

3.0 grams polyvinylpyrrolidone (PVP).

sodium bicarbonate and sodium chloride to result in physiologic starting concentrations in the dialysate sorbent suspension after priming (sodium=140 mEq/L, bicarbonate=35 mEq/L, chloride=105 mEq/L).

The priming fluid for the blood side of the dialysis system was one liter of 5% dextrose from container 42 attached to blood inflow tube 24 via tube 23. During priming, priming/rinse clamp automatically opens prime tube 23 while closing blood inflow tube 24. Priming fluid is thus pulled into the system rather than blood. Glucose passes across the membranes of the dialyzer 30, and 20 grams binds to the charcoal, while sodium chloride, and bicarbonate pass from the suspension into the priming fluid. During dialysis, glucose disassociates from the charcoal and returns to the patient (unless the patient's glucose is very high). A reinfusate of sterile calcium chloride and potassium chloride was pumped by reinfusate pump 58 from reinfusate container 41 through tube 26 into the outflow line 25 at a diminishing rate throughout the treatment, to offset removal by the cation exchanger.

The system also includes a variety of sensors to make operation safe, simple and highly automated, including:

a scale to weigh the entire top of the machine, to measure volumes ultrafiltered from and returned to the patient;

blood sensors (54 and 56) to measure foam, bubbles, particles of blood in the inflow and outflow lines 24 and 25, and to measure flow rate on the inflow line 24;

hemoglobin sensor 46 to chemically detect hemoglobin within the sorbent suspension if there is a membrane blood leak. For this function, a filtrate collector 47 provides a solid-free sample of the dialysate fluid to hemoglobin sensor tape which changes color if hemoglobin is present. The tape is automatically wetted with samples of dialysate, advanced and monitored for color change by a reflectometer. The wetting of the tape is controlled by filtrate pump 63 which further pumps excess filtrate via tube 31 into collection container 32.

empty line sensors on all fluid-filled lines;

temperature sensor for fluid in the reservoir tank 13 surrounding the sorbent bag 15 (optimally heated to about 37° to 40° C. by heating elements also provided in the machine).

The computers of the system automate many of the steps of treatment, including:

priming of the machine, observing lines to determine that all air is removed;

returning fluid to the patient when desired final weight is obtained or on command (for the latter, automatically adjusting ultrafiltration to reach desired final weight).

rinsing the dialyzer and blood lines at the end of treatment; and recording, storing and transferring data concerning progress of each treatment.

EXAMPLE 2

Treatment of Hepatic Failure

Patient Selection

For patients with hepatic failure the following criteria were requisite for treatment by the inventive method:

acute hepatic failure, with a history of normal liver status, or of stable liver insufficiency and sudden deterioration;

a potential for recovery of liver function by any means (removal of etiologic agent, correction of coexisting diseases and complications, surgical treatment of the hepatic disease, regeneration of injured hepatic tissue or liver transplant);

elevated serum ammonium, protime, and other markers of hepatic insufficiency;

stage 3 (incoherence/sleep) or 4 (unresponsiveness) coma apparently due to hepatic failure, with declining clinical condition;

informed consent by patient or family.

Treatment Protocol

Patients meeting the above criteria were treated each day with the system of Example 1, for periods of 8-12 hours, each treatment using a single pack of sorbent materials. The blood access was a single-lumen 8 French catheter in the femoral vein or subclavian vein, left in place between treatments (heparin-locked). Treatments were performed daily until one of the following occurred: intrinsic liver function returned and the patient returned to reasonable health, a liver transplant was performed, a total of 12 treatments were performed, or the appearance or progress of several coexisting diseases made eventual patient survival unlikely.

Since all patients had some degree of coagulopathy, the protocol included no anticoagulation. During each treatment, the optic monitors of the system automatically and frequently measured the blood treatment rate. If, during the first few hours of treatment, the blood flow fell from the starting level of 180-225 ml/min to 120 ml/min, then the treatment was discontinued or 1000 units of heparin were administered and the treatment continued (this occurred in a total of 4 treatments). 49 treatments were completed without administering any anticoagulant. In many treatments, the activated clotting time (ACT) of inflowing blood was measured each hour. The ACT level always diminished towards normal during treatments, even when other clotting tests (PT and PTT) increased slightly. A low ACT level was not found to be a reliable indication of need for anticoagulation.

Neurologic and Physiologic Status Evaluation

For a four hour period before each treatment, five clinical signs were carefully evaluated by nurses caring for the patient: systolic blood pressure, diastolic blood pressure, pulse, temperature, and neurologic status. The neurologic status was quantified using the six-sign analysis and score developed by Coronna (See *J. Pharm. Pharmacol.*, 40, 318-87 (1988)) and recommended by Jones for evaluation of hepatic coma (See *Trans. Am. Neurol. Assoc.*, 100, 25 (1975)). The score includes the three elements of the Glasgow score, plus evaluation of pupils, oculocephalic reflex, and respiration status. To this was added a ranking of tremor from 1-4, thus making the total score for normal status equal to 27.

A similar four-hour evaluation was performed after discontinuation of each treatment. Review of chart records allowed quantitation of patient status in the days prior to the first treatment, and in some cases long after the last treatment.

Statistical analysis of clinical data began with averaging each measured parameter over the four-hour observation period. The acute change in each parameter during each treatment was calculated by subtracting the pre- and post-treatment levels. The mean change per treatment for all patients was then calculated, and the T-test used to determine whether the change in status was different from zero. In addition, the trend of each parameter (rate of change per day) was calculated by least squares regression, for the days prior to treatment, days of treatment, and days after treatment. The change in this slope at beginning and end of the treatment period was calculated. The paired T test was used to determine whether there was a change in slope at these times.

FIG. 1 presents the average change in neurologic status during individual treatments and in the days before, during, and after treatment in accordance with the invention. Prior to treatment the total neurologic score was declining at a rate of $-3.19$ points per day (d/day pre). During each treatment the score increased by 1.99 points (d/rx, $p<0.01$). In the days following discontinuation of treatment, the average score decreased at $-0.03$ points/day (d/day post, $p<0.01$). The average age of patients was 44, the stage of coma at start of treatment averaged 3.9 (median, 4), and 11 patients were on respirators. Kidney failure had followed hepatic failure in 11 patients. Neurologic improvement occurred during treatments in 13 patients, and physiologic improvement in 13.

Before treatment, the average blood pressure and temperature were low, and pulse high. During treatments, all patients were physiologically stable. The only significant changes during treatment were a slight increase in diastolic blood pressure (3 mm, $p=0.04$) and a slight decrease in pulse rate ($-3$ beats/min/day during days of treatment, $p=0.04$).

In spite of the severity of illness, instability and complexity of these patients, there were no adverse symptoms or adverse physiological changes during the treatments. One treatment was purposefully discontinued early, this in a patient with bronchitis and intermittent respiratory distress before treatment which recurred during one treatment. This patient eventually received a successful liver and kidney transplant.

EXAMPLE 4

TREATMENT OF OVERDOSE

A 29 year-old patient willfully ingested an overdose (about 3 times the lethal dose) of amitriptyline, a tricyclic antidepressant that is greater than 90% protein bound. Prior to treatment according to the invention, the patient was given all known conservative therapies, yet the patient's clinical condition continued to decline. Just prior to treatment the patient was in Stage 3-4 coma (little response to pin stick) and on a respirator. The patient was thereafter treated for four hours in accordance with the invention, using the system described in Example 1 above. One and one half hours into the treatment, the patient became more alert (even made some notes) and after two hours the respirator was removed. At the end of the treatment the patient was essentially fully alert, and was subsequently released from the hospital. It was thus demonstrated that the method of the invention can be used to treat drug overdose and result in dramatic improvement of the patient's condition even when the drug is highly protein bound.

EXAMPLE 5

PULSE THERAPY—METHOTREXATE

The purpose of this example was to determine the capacity of the inventive method to remove Methotrexate from the blood of patients on high dose therapy or in cases of overdosage. Methotrexate has a molecular weight of 455, and is an analog of the vitamin folic acid. Acting as an antimetabolite, Methotrexate inhibits DNA and RNA synthesis so as to impair cell proliferation. It has a wide spectrum of clinical indications in the treatment of neoplastic diseases and is also used in severe, recalcitrant psoriasis. It is primarily eliminated from the body by renal excretion. Serious adverse reactions occur in all tissues where there is active cell proliferation. Toxic effects are related to dose and to the body's ability to excrete the drug. To diminish toxic effects, leucovorin is sometimes used in a rescue procedure when very high doses of Methotrexate are employed, in combination with other anti-cancer agents, for example in the treatment of osteosarcoma.

To 1.7 liters of cow blood, containing EDTA as an anti-coagulant, were added 38.7 milligrams of Methotrexate to achieve a final plasma concentration of 64 micromoles/liter. The blood was then treated essentially with a system as described in Example 1. The blood was treated for one hour at a treatment rate of 260 ml/min. Blood samples were taken at ten minute intervals, and plasma samples were obtained immediately from the blood samples by centrifugation at 4° C. Supernate samples were taken from the sorbent suspension at the beginning and the end of the treatment. The blood and supernate samples were assayed for concentration of Methotrexate. The average clearance over the hour of treatment was 74.4 ml/min. The ending plasma concentration of Methotrexate was 4.9 micromoles/liter, which represented a 92% reduction in 55 minutes. The ending supernate concentration of Methotrexate was 0.02 micromoles/liter. It was thus demonstrated that the inventive drug removal system may be used as an alternative to leucovorin for limiting or counteracting Methotrexate toxicity when high dose therapy is used or when the body fails to clear the drug fast enough.

EXAMPLE 6

PULSE THERAPY—CISPLATIN

Another experiment was conducted to determine the capacity of inventive method to remove Cisplatin from a patient's blood.

Cisplatin (Plantinol ® by Bristol Laboratories) is a heavy metal complex of platinum, chloride and ammonia with a molecular weight of about 300. Following a single I.V. dose, Cisplatin concentrates in the liver, kidneys, and large and small intestines. Plasma levels of Cisplatin decay in a biphasic manner. The initial plasma half-life is 25 to 49 minutes, and the post-distribution plasma half-life is 58 to 73 hours. It is highly protein bound (90%) and is primarily excreted in the urine. However, urinary excretion is incomplete, with only 27% to 43% of the Cisplatin being excreted within the first five days post dose. Cisplatin is indicated for metastatic testicular tumors (in combination with bleomycin and vinblastine), metastatic ovarian tumors (in combination with doxorubicin), advanced bladder cancer, non-Hodgkin's lymphoma, and head and neck cancers. Severe toxicities include intractable nausea and vomiting, cumulative renal impairment and ototoxicity (initially as reversible high frequency hearing loss progressing to permanent deafness).

Preliminary charcoal binding studies showed that at least 50–100 milligrams of Cisplatin would be expected to be bound by 140 grams of charcoal (the amount of charcoal used in the system of Example 1) with a concentration of free Cisplatin in the fluid around the charcoal particles (the supernate) of less than 5 micrograms/ml. The ability of the sorbent to bind this amount of drug while maintaining a low concentration of unbound drug in the fluid phase is an important requisite if the inventive method is to effectively remove drug from the blood where it is highly bound to proteins.

In the blood study, Example 5 was repeated, except using Cisplatin instead of Methotrexate. Accordingly, sufficient Cisplatin was added to 1.7 liters of cow blood (oxygen tension and temperature constant) to achieve a final Cisplatin concentration of 28 micrograms/ml. The blood was then treated with a system as described in Example 1, at a blood treatment rate of 260 ml/min. The treatment duration was one hour. Blood samples were taken at ten minute intervals, and plasma samples were obtained therefrom by centrifugation at 4° C. Supernate samples were taken from the sorbent suspension at beginning and end of the treatment period. The blood and supernate samples were assayed for Cisplatin (by atomic absorption spectroscopy). The ending plasma concentration was 4.2 micrograms/ml, which represented an 85% reduction in one hour. The ending supernate Cisplatin concentration was 2 micrograms/ml. The average Cisplatin clearance over the one hour treatment period was 39 ml/min.

It was thus demonstrated that the inventive drug removal system may be used for limiting or counteracting Cisplatin toxicity when high dose therapy is used.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A method for extracorporeal treatment of blood to effectively and consistently remove toxins therefrom over an extended period of time, comprising:
    passing the blood through a blood side of a plate dialyzer having a blood inlet to and a blood outlet from a blood side separated from a dialysate side by dialyzer membranes, said plate dialyzer further having a dialysate inlet to and dialysate outlet from said dialysate side, said dialyzer membranes being compliantly formed to expand and compress in response to alternating negative pressure and positive pressure on said dialysate side of said dialyzer; and
    passing a sorbent suspension through said dialysate side so as to dialyze toxins in the blood across the membranes;
    wherein said passing steps are caused by the application of alternating negative and positive pressure on said dialysate side so as to expand and contract said membranes and agitate the sorbent suspension to prevent settling and maintain chemical gradients across the membrane, while also maintaining a positive pressure gradient from said blood side to said dialysate side; and
    wherein said alternating negative and positive pressure are caused by an accumulator reservoir connected to said dialysate side and operable to alternatively accumulate and expel dialysate.

2. The method of claim 1 wherein the sorbent suspension is an aqueous suspension including powdered activated charcoal.

3. The method of claim 2 wherein the charcoal has an average particle diameter of less than about 75 microns.

4. The method of claim 3 wherein said treatment is of blood of a patient having hepatic failure.

5. The method of claim 3 wherein said treatment is of blood of a drug overdose patient.

6. The method of claim 3 and also including the step of:
    administering a dose of therapeutic agent to a patient;
    and wherein said treatment is of blood of said patient following said administering and is effective to remove said thereapeutic agent.

7. The method of claim 3 wherein the sorbent suspension also comprises a cation exchanger.

8. The method of claim 7 wherein the sorbent suspension also comprises polyvinylpyrrolidone and a polyol flow inducing agent.

9. The method of claim 7 wherein said treatment is of blood of a patient having hepatic failure.

10. The method of claim 7 wherein said treatment is of blood of a drug overdose patient.

11. The method of claim 3 wherein the sorbent suspension also comprises polyvinylpyrrolidone and a polyol flow inducing agent.

12. The method of claim 11 wherein said treatment is of blood of a patient having hepatic failure.

13. The method of claim 11 wherein said treatment is of blood of a drug overdose patient.

14. A dialysis instrument, comprising:
    a plate dialyzer having a blood inlet to and a blood outlet from a blood side separated from a dialysate side by dialyzer membranes, said plate dialyzer further having a dialysate inlet to and dialysate outlet from said dialysate side, said dialyzer membranes being compliantly formed to expand and compress in response to alternating negative pressure and positive pressure on said dialysate side of said dialyzer;
    dialysate circulating means for circulating dialysate through said dialysate side of said dialyzer in a direction generally from said dialysate inlet to said dialysate outlet;
    said dialysate circulating means including an accumulator reservoir operable to alternately accumulate and expel dialysate to apply alternating negative pressure and positive pressure on said dialysate side of said dialyzer and to thereby cause said expansion and contraction of dialyzer membranes while maintaining a positive pressure gradient from said blood side to said dialysate side of said dialyzer;
    blood circulating means for circulating blood through said blood side of said dialyzer in a direction generally from said blood inlet to said blood outlet and powered by said expansion and contraction of dialyzer membranes caused by alternating negative and positive pressure on said dialysate side of said dialyzer.

15. The dialysis instrument of claim 14 which includes:
    a dialysate storage reservoir;
    first conduit means for fluidly connecting said dialysate reservoir to said dialysate inlet of said dialyzer;
    second conduit means for fluidly connecting said dialysate reservoir to said dialysate outlet of said dialyzer;
    a one-way valve in said second conduit means which allows flow only toward said dialysate storage reservoir;
    and wherein said accumulator reservoir is fluidly connected to said second conduit means between said one-way valve and said dialysate outlet of said dialyzer so that dialysate expelled from said accumulating reservoir passes partially back into said dialysate side of said dialyzer and partially to said storage reservoir.

16. The dialysis instrument of claim 15 wherein said dialysate storage reservoir contains materials that are in a dry state, but which will form a dialysate sorbent suspension upon the addition of water.

17. The dialysis instrument of claim 14 wherein said dialysate circulating means includes a dialysate storage reservoir coupled to the dialysate inlet; and wherein said accumulator reservoir is connected between said dialysate outlet and said dialysate storage reservoir.

18. The dialysis instrument of claim 17 wherein a one way valve allowing dialysate flow toward said dialysate storage reservoir is located between said dialysate accumulating reservoir and said dialysate storage reservoir so that dialysate expelled from said accumulating reservoir passes partially into said dialysate side of said dialyzer and partially to said storage reservoir.

19. The dialysis instrument of claim 18 wherein said accumulator reservoir comprises a container having a port located above the maximum level to which dialysate accumulates in said container, through which negative and positive pressure can be alternately applied to cause said accumulation and expellation of dialysate into and from said container.

20. The dialysis instrument of claim 19 and also including means for alternately applying positive and negative pressure to said port.

21. The dialysis instrument of claim 20 which is adapted to cause counter-current flow of said dialysate and said blood.

* * * * *